United States Patent
Abatangelo et al.

(10) Patent No.: US 6,596,274 B1
(45) Date of Patent: Jul. 22, 2003

(54) BIOLOGICAL MATERIAL CONTAINING BONE MARROW STEM CELLS PARTIALLY OR COMPLETELY DIFFERENTIATED INTO CONNECTIVE TISSUE CELLS AND A HYALURONIC ACID ESTER MATRIX

(75) Inventors: Giovanni Abatangelo, Saccolongo (IT); Lanfranco Callegaro, Thiene (IT)

(73) Assignee: Fidia Advanced Biopolymers S.r.l., Brindisi (IT)

(*) Notice: Subject to any disclaimer, the term of this patent is extended or adjusted under 35 U.S.C. 154(b) by 0 days.

(21) Appl. No.: 09/041,287

(22) PCT Filed: Nov. 19, 1996

(86) PCT No.: PCT/EP96/05093

§ 371 (c)(1), (2), (4) Date: Mar. 12, 1998

(87) PCT Pub. No.: WO97/18842

PCT Pub. Date: May 29, 1997

(30) Foreign Application Priority Data

Nov. 20, 1995 (IT) .......................... PD95A0225

(51) Int. Cl.[7] .............. A61F 2/00; A01N 1/00; A01N 65/00; C12N 5/00; C12N 11/02
(52) U.S. Cl. .............. 424/93.7; 424/423; 435/1.1; 435/177; 435/325; 435/372; 435/395
(58) Field of Search .............. 435/325, 1.1, 174, 435/284.1, 372, 395, 177; 424/93.7, 423

(56) References Cited

U.S. PATENT DOCUMENTS 5,510,254 A * 4/1996 Naughton et al. ..... 435/240.243
5,776,193 A * 7/1998 Kwan et al. .................. 623/16

OTHER PUBLICATIONS

Department of Biology, Massachusetts Institute of Technology, pp. 1–12, "Serial Cultivation of Strains of Human Epidermal Keratinocytes: The Formation of Keratinizing Colonies from Single Cells"; James G. Rheinwald et al. received 1975.

The New England Journal of Medicine, vol. 311, No. 7, pp. 448–451 (1984); "Permanent Coverage of Large Burn Wounds with Autologous Cultured Human Epithelium", G. Gregory Gallico et al.

Science, Vo. 215, pp. 174–176 (1982): "Wound Tissue Can Utilize a Polymeric Template to Synthesize a Functional Extension of Skin", I. V. Yannas et al.

Surgery, vol. 103, No. 4, pp. 421–431 (1988); "Biologic Attachment, Growth, and Differentiation of Cultured Human Epidermal Keratinocytes on a Graftable Collagen and Chondroitin–6–Sulfate Substrate", Steven T. Boyce, Ph.D. et al.

Biomaterial, vol. 14, No. 15, pp. 1154–1160 (1993); "Biocompatibility and Biodegradation of Different Hyaluronan Derivatives (HYAFF) Implated in Rats", L. Benedetti et al.

Biomaterials, 12, pp. 727–730 (1991); "In Vitro Studies on Biocompatibility of Hyaluronic Acid Esters", E. Cortivo et al.

* cited by examiner

Primary Examiner—David M. Naff
Assistant Examiner—Deborah K. Ware
(74) Attorney, Agent, or Firm—Hedman & Costigan, P.C.

(57) ABSTRACT

A biological material comprising two components is provided containing a first component comprising alternatively (1) a culture of autologous or homologous bone marrow stem cells partially or completely differentiated into specific connective tissue cellular lines or (2) a sole extracellular matrix free from any cellular component secreted by the specific connective tissue cellular lines; and a second component containing a three-dimensional biocompatible and biodegradable matrix consisting of a hyaluronic acid ester having a degree of esterification comprised between 25 and 100%. The specific tissue cell lines are selected from fibroblasts, osteoblasts, myoblasts, adipocytes, chondrocytes and endothelial cells. The biological material is suitable for use as a dermal substitute in cutaneous lesions as well as repairing damaged connective tissue.

19 Claims, 5 Drawing Sheets

BIOLOGICAL MATERIAL CONTAINING BONE MARROW STEM CELLS PARTIALLY OR COMPLETELY DIFFERENTIATED INTO CONNECTIVE TISSUE CELLS AND A HYALURONIC ACID ESTER MATRIX

FIELD OF THE INVENTION

The present invention relates to a biologic material, a process for its preparation and the use thereof in tissue grafts.

BACKGROUND OF THE INVENTION

The loss of cutaneous material due to various causes, traumatic or metabolic for example, can sometimes prove to be very slow-healing. This can be due to metabolic or local circulatory causes, the patient's poor state of health or to the size of the wound, as in the case of extensive burns. The ineffectiveness of pharmacological therapy has led physicians to resort to reconstructive surgery, using skin grafts from the same patient whenever possible. An important breakthrough in the treatment of such lesions is the use of techniques for in vitro cell culture.

Another problem involved in the preparation of skin substitutes is represented by the supply of fibroblasts to seed onto the biocompatible matrices. Indeed, it is not always easy to isolate fibroblasts from dermal tissues, especially in the case of elderly or severely weakened subjects. One solution to this problem is offered by the mesenchymal cells present in bone marrow tissue. These cells are very active and can be suitably differentiated into various cell lines when placed in the correct conditions. From these stem cells it is possible to obtain differentiated cells such as fibroblasts, adipocytes, myoblasts, osteoblasts, chondrocytes.

J. Rheinwald and H. Green (Cell, 6, 1975, 331–344) were the first to cultivate keratinocytes which could be successfully used to cover skin lesions in clinical practice (G. G. Gallico et al., N. Engl. J. Med., 311, (1984), 448–451). This innovative technique proved to have its limits, however, the most serious being the extreme fragility of the epithelial layer and the very low take rate. To overcome these limitations, dermal derivatives have been constructed on which keratinocytes can be grown. Yannas et al. (Science, 215, (1982), 174–176) used a mixture of collagen and glycosaminoglycans to obtain a reabsorbable porous material to serve as a skin substitute on lesions characterised by the loss of cutaneous substance.

S. Boyce and J. Hansbrough (Surgery, 103 (1988), 421–431) described the use of layers of collagen and glycosaminoglycans as supports on which to grow keratinocytes for subsequent graft.

Another system for the preparation of dermal substitutes is represented by fibroblast cultures on biocompatible three-dimensional matrices based on synthetic or semisynthetic polymers. It is possible to seed and grow fibroblasts on these structures, thus enabling the production of an extracellular matrix similar to that of natural connective tissue.

Some well-known examples of dermal substitutes are:

1) Dermagraft, developed by Advanced Tissue Science (California), in which human fibroblasts are seeded and cultivated on a matrix formed by polylactic, polyglycolic or polygalactoside acid. These fibroblast-populated matrices are subsequently seeded with keratinocytes, to enhance their more "physiological" growth;

2) Graft-skin, by Organogenesis Inc. (Boston U.S.A.) composed of a collagen substrate on which heterologous human fibroblasts are seeded;

3) AlloDerm, produced by Life Cell Corp. (Texas, U.S.A.), constituted by human or pig dermis, left intact and stored at a low temperature. Before use, it can be seeded with autologous fibroblasts and keratinocytes and then used for grafting.

Although these products represent good biological supports for in vitro cultures, their in vivo application is somewhat limited, due to immunological reactions against their non-autologous protein components, as well as to the risk of viral contamination.

Lastly, other products deriving from hyaluronic acid are known to be used in skin grafts thanks to their highly biocompatible and biodegradable materials (Benedetti et al., Biomaterials, 14 (1993) 1154–1160; Cortivo R. et al., Biomaterials, 12 (1991) 727–730) and their lack of immunoreactivity. Indeed, as hyaluronic acid is a component of the extracellular matrix it releases completely natural fragments during its degradation in the tissues.

SUMMARY OF THE INVENTION

The present invention relates to a biologic material comprising the following two components:

a) an efficient culture of autologous or homologous bone marrow stem cells partially or completely differentiated into cellular lines of a specific connective tissue and further comprising the extracellular matrix produced by said connective tissue cells, or alternatively a') the extracellular matrix secreted by:
bone marrow stem cells partially or completely differentiated into a specific connective tissue, or alternatively,
the specific homologous mature connective tissue cells, said extracellular matrix being free from any cellular component, and b) a three-dimensional biocompatible and biodegradable matrix consisting of a hyaluronic acid derivative.

The present invention further relates to the processes for preparing said biologic material.

When the biologic material according to the present invention contains the component (a) or the component (a') being the extracellular matrix secreted by connective tissue cells coming from partial or complete differentiation of bone marrow stem cells, the process comprises the following steps:

i) isolating said homologous or autologous stem cells from the bone marrow.

ii) transferring said isolated stem cells onto said biocompatible three-dimensional matrix consisting of a hyaluronic acid ester, and iii) growing and developing said stem cells upon and inside the biomaterials, by dipping the biologic material coming from the preceding step in a culture medium containing also a differentiating factor in case the desired connective tissue cells are different from fibroblasts, thereby obtaining the biologic material containing the component (a), and optionally iv) removing the homologous cellular component of (a), by osmotic lysis, thereby obtaining the biologic material containing the above mentioned component (a').

The process for preparing the biologic material according to the present invention containing the component (a') secreted by mature specific connective tissue cells comprises the following steps:

(i') isolating said mature cells from the specific connective tissue, and growing them under conventional and specific growth condition depending on the specific mature connective cells (ii') transferring said mature connective tissue cells onto said three dimensional matrix consisting of said hyaluronic acid derivative, iii') growing and developing said connective tissue cells upon and inside said three dimensional matrix, iv') removing by means of osmotic lysis the cellular components.

The present invention further relates to the use of said biologic material in tissue grafts.

BRIEF DESCRIPTION OF THE FIGURES

FIG. 1: represents the immunohistochemical marking of Collagen I with monoclonal antibodies (avidin/biotin,; 200×) of:

A: HYAFF$^R$ 11 non woven tissue in which human fibroblasts from bone marrow mesenchyma have been seeded. After 2 weeks culture the presence of type I collagen can be observed.

B: HYAFF$^R$11 containing human fibroblasts of dermal origin. In this case too, there is a definite positivity for collagen I.

Figure 1A:
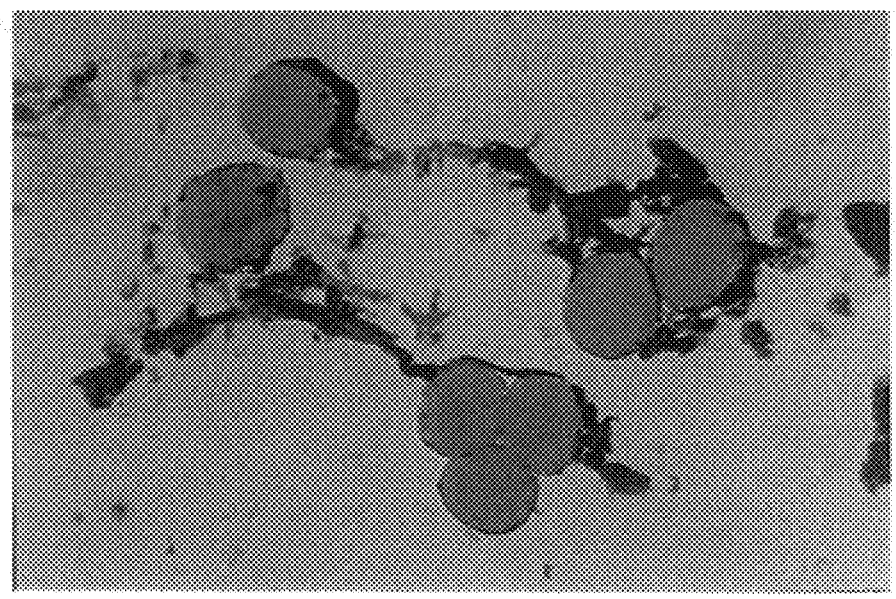
Figure 1B:
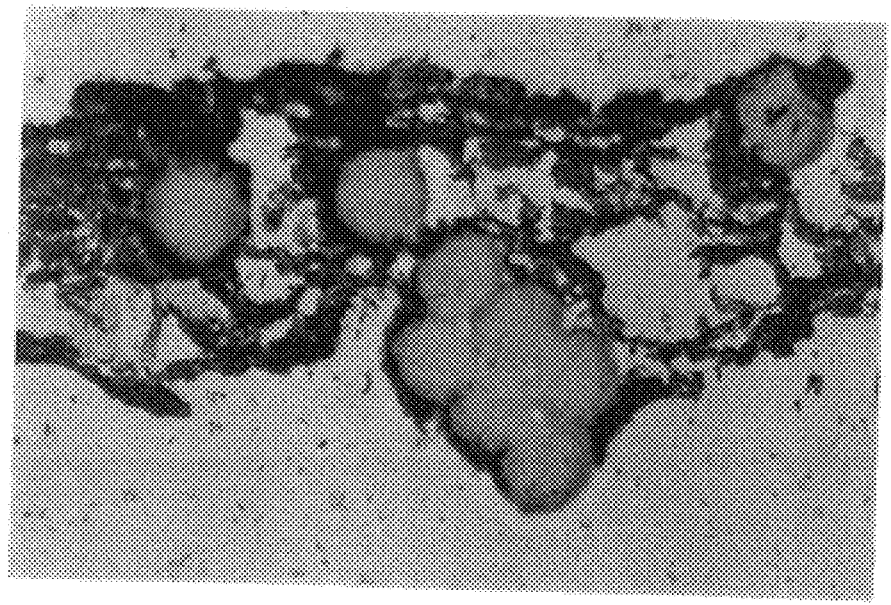
Figure 2A:
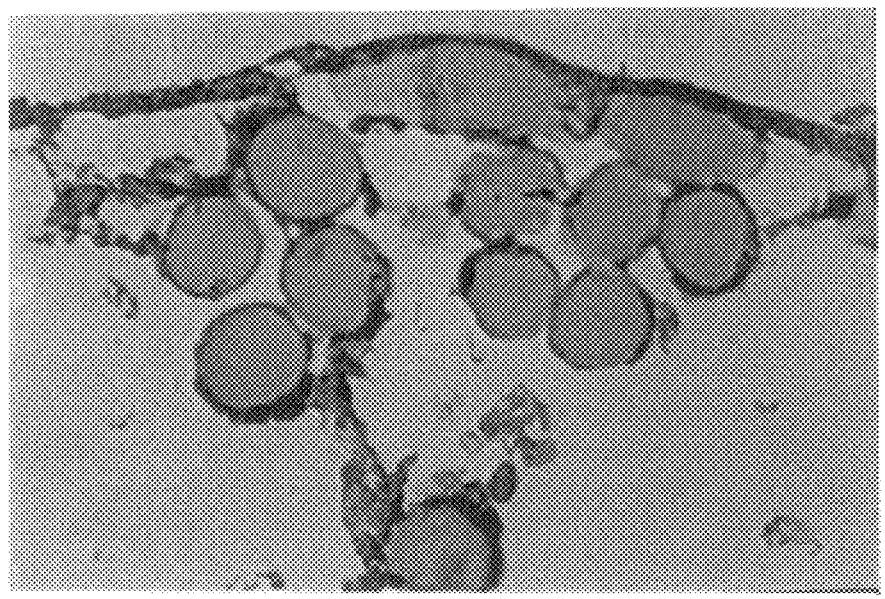
Figure 2B:
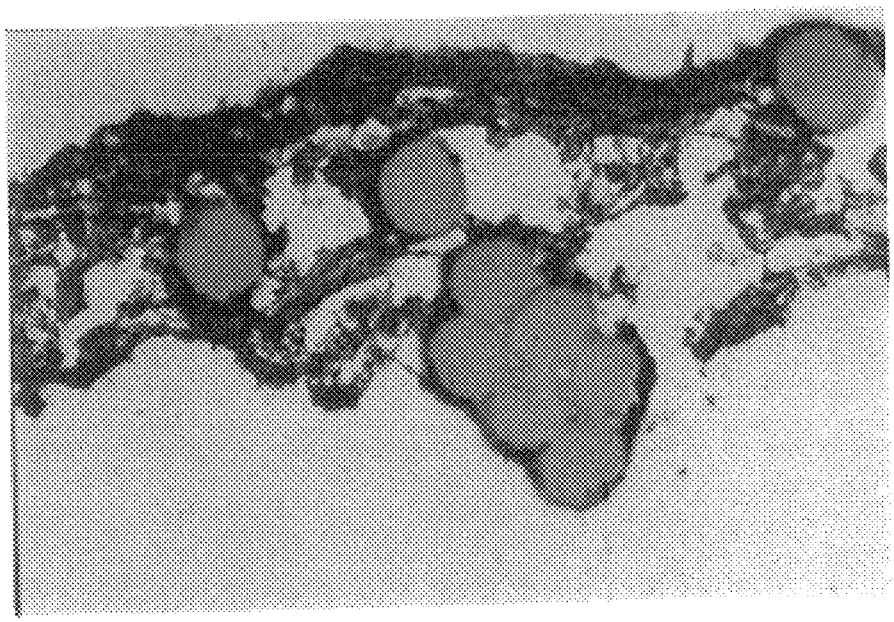

FIG. 2: represents the himmunohistochemical marking of collagen III with monoclonal antibodies (avidin/biotin; 200×) of:

A: HYAFF$^R$-11 with bone marrow mesenchymal fibroblasts 2 weeks after seeding, there is marked positivity to the reaction.

B: HYAFF$^R$-11 with fibroblasts of dermal origin 2 weeks after seeding, there is marked positivity to the reaction.

Figure 3A:
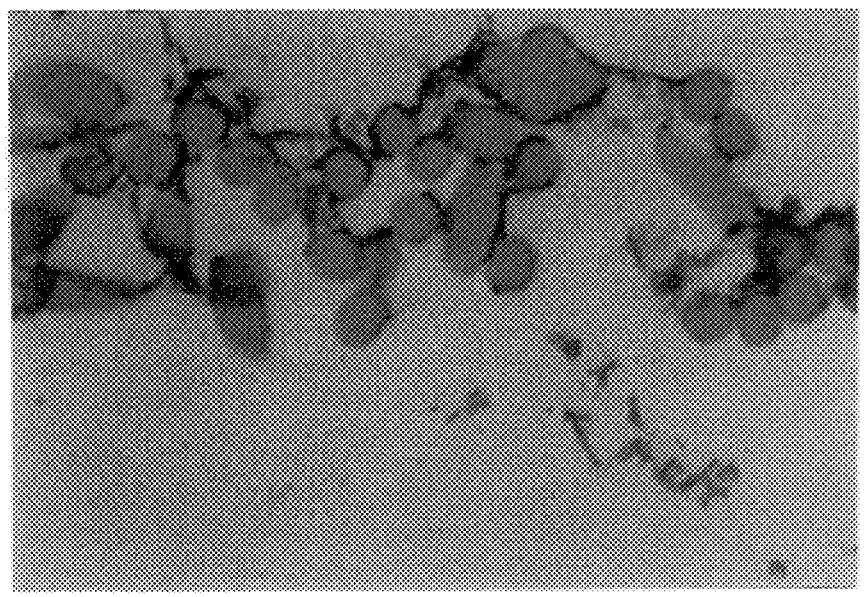
Figure 3B:
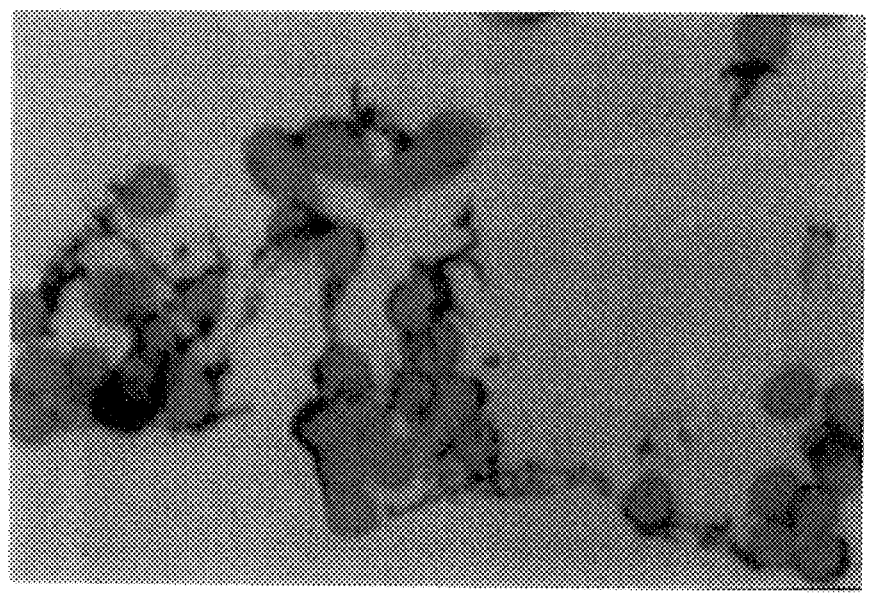

FIG. 3: represent the immunoreaction with anticollagen IV antibodies (avidin/biotin; 100×) of:

A: HYAFF$^R$-11 with bone marrow mesenchymal fibroblasts 2 weeks after seeding

B: HYAFF$^R$-11 with dermal fibroblasts after 2 weeks in culture

The two different types of fibroblasts express collagen IV synthesis in the same manner.

Figure 4A:
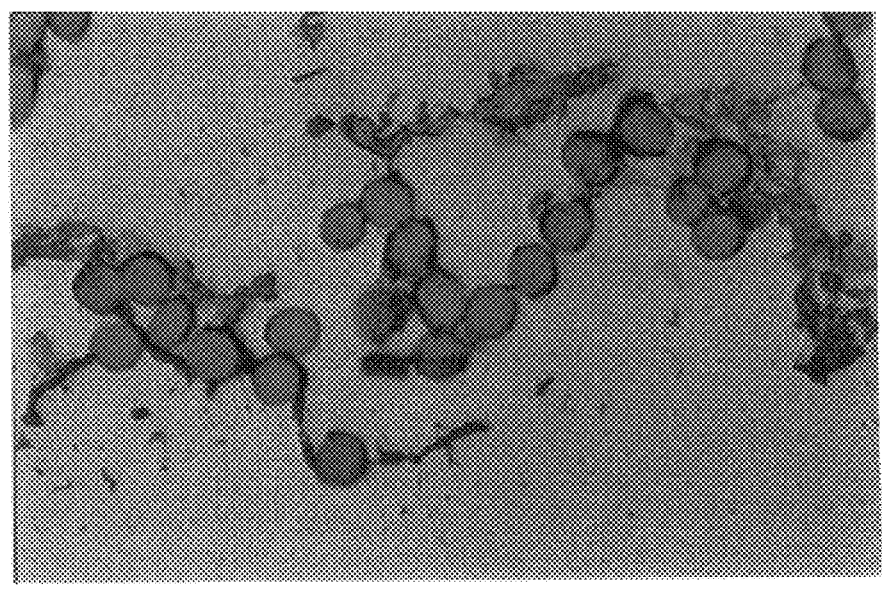
Figure 4B:
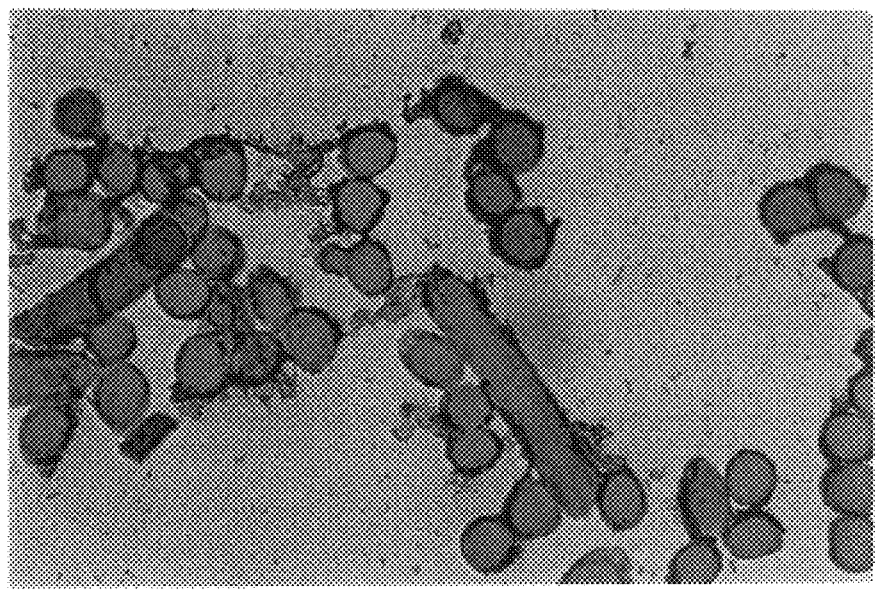

FIG. 4: represents immunohistochemical marking of fibronectin with monoclonal antibodies (avidin/biotin 100×) of:

A: HYAFF$^R$-11 with fibroblasts from bone marrow 2 weeks after seeding

B: HYAFF$^R$-11 with fibroblasts of dermal origin after 2 weeks in culture

Positivity to immunoreaction is marked in both types of fibroblast.

Figure 5A:
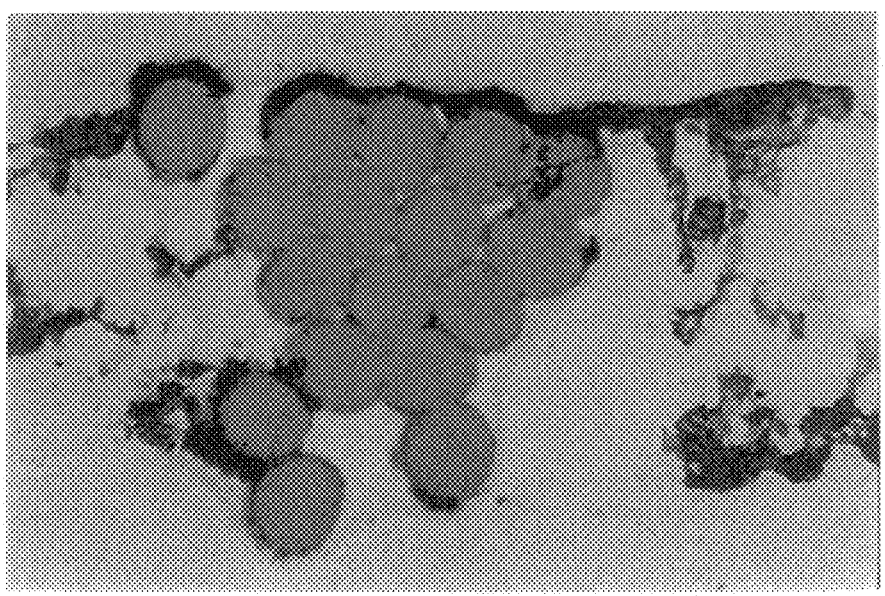
Figure 5B:
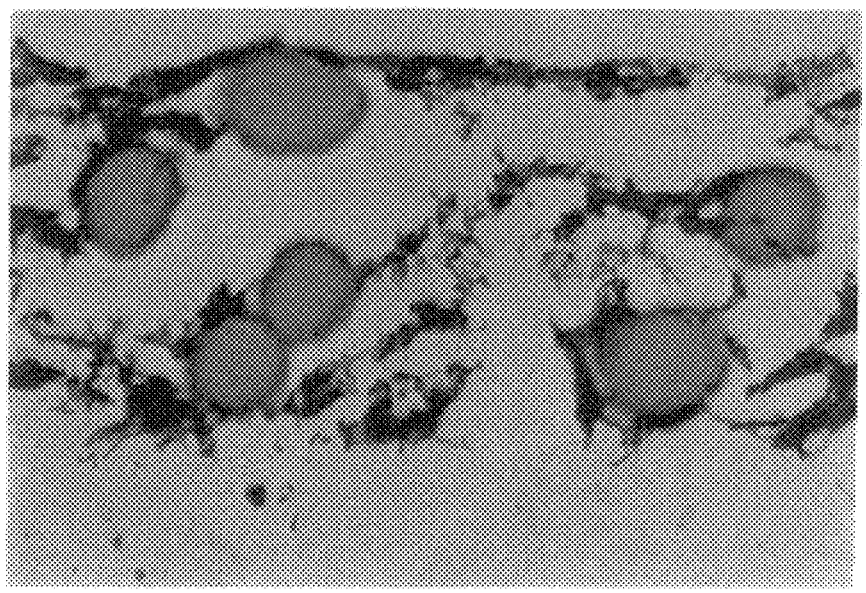

FIG. 5: Immunohistochemical marking of laminin with monoclonal antibodies (avidin/biotin; 200×)

A: HYAFF$^R$-11 with fibroblasts from bone marrow 2 weeks after seeding,

B: HYAFF$^R$-11 with dermal fibroblasts 2 weeks after seeding

The presence of laminin is very clear in both types of cultures.

DETAILED DESCRIPTION OF THE INVENTION

Preferably the hyaluronic acid derivative forming the three dimensional matrix of the biologic material according to the present invention is a hyaluronic acid ester like those disclosed in U.S. Pat. No. 4,851,521. which we incorporate by reference.

More preferably the hyaluronic acid ester is the benzyl ester having a degree of esterification varying from 25 to 100%.

According to a particular preferred embodiment hyaluronic acid benzylesters are used whose degree of esterification is respectively 75% (HYAFF$^R$-11p75) and 100% (HYAFF$^R$11).

The three-dimensional matrix consisting of a hyaluronic acid derivative are preferably in the form of non woven tissue, sponges, granules microspheres guide channels and gauzes.

According to a particularly preferred embodiment the three-dimensional biocompatible matrix of the biologic material according to the present invention are preferably in the form of a non woven-tissue.

The preparation of said non woven tissue consisting of a hyaluronic acid derivative and in particular of the ester of hyaluronic acid esters is disclosed in U.S. Pat. No. 5,520,916, which we incorporate herewith by reference.

The specific connective tissue cells, coming from the complete or partial differentiation of bone marrow stem cells contained in (a), in the biologic material according to the present invention, are preferably selected from the group consisting of fibroblasts, osteoblasts, myoblasts, adipocytes, chondrocytes and endothelial cells.

Therefore, when (a) comprises chondrocytes, being able able to form a chartilage tissue, the biologic material according to the present invention can be used for covering areas of eroded or degenerated chartilage.

When (a) comprises osteoblasts, being able to form a bone tissue, the biologic material according to the present invention can be used in case of loss of bone substance.

When (a) comprises fibroblasts, the biologic material of the present invention is grafted onto the damaged skin, (b) is absorbed within a given length of time thanks to its biodegradability, thus leaving newly-formed dermal tissue at the site.

When autologous connective, tissue cells have been seeded on the matrix consisting of the hyaluronic acid derivative, they can remain in the newlyformed connective tissue and contribute towards wound repair by means of the various growth factors and extra cellular matrix they secrete.

In case connective tissue coming from partial or complete differentiation of homologous bone marrow stem cells or homologous mature connective tissue are only available, the Applicant has found that with the biologic material containing the component (a') in place of component (a), it is possible to avoid undesired immunological reaction.

Therefore according to a preferred embodiment the connective tissue cells producing the extracellular matrix in this biologic material may derive from homologous partially or completely differentiated stem cells of bone marrow or from homologous mature connective tissue. The homologous mature connective tissue cells secreting component (a') are selected from the group consisting of fibroblasts, osteoblasts, myoblasts, adipocytes, chondrocytes and endothelial cells.

Mature fibroblasts may be isolated by dermal tissue coming either from autopsy or from biopsy, mature chondrocytes from autopsy chartilage, mature osteoblasts coming from biopsy fragments of bone tissue, mature muscular cells from biopsy fragments of muscular tissue, mature endothelial cells from biopsy fragments of small vasa or from dermis itself, mature adipocytes from biopsy fragments of adipous tissue.

Therefore the biologic material according to the present invention containing the component (a') can be used for the same purposes as those contemplated for the biologic material containing the component (a).

In particular the biologic material according to the present invention both in the case it comprises (a), containing fibroblasts coming from partial or complete differentiation of bone marrow stem cells and in the case it contains (a'), secreted either by homologous or mature fibroblasts or by fibroblasts deriving from homologous partially or completely differentiated stem cells, can serve as a substrate for the in vitro seeding of autologous or homologous keratinocytes for subsequent graft.

This biologic materials is suitable for use as a dermal substitute in cutaneous lesions where substance has been lost In the process for respectively preparing the biologic materials containing the component (a) or alternatively the component (a'), secreted by homologous connective tissue cells obtained by partial or complete differentiation of bone marrow stem cells, step (i) preferably comprises the following operating conditions:

1) aspirating the bone marrow from the iliac crest or head of the femur;
2) treating the liquid coming from step (1) in the presence of Hank's saline solution at +4° C. and centrifuging the mixture thus obtained,
3) removing by aspiration the supernatant and the lipid layer,
4) removing erythrocytes in excess by using Percoll or Ficoll gradients, thereby obtaining the mesenchymal cells fraction,
5) centrifuging the mesenchymal fraction and recovering the solid;
6) resuspending the solid in a culture medium containing α-MEM supplemented with 10% foetal calf serum. 1% L-glutamine 200 mM, 1% penicillin/streptomycin 10,000U/10,000 µg/ml;
7) seeding in a Petri dish at a density of 50–100×10$^6$ nucleate cells/dish;
8) incubating the cells in the medium for 72 hours and changing the medium to remove the non adhered cells.

Step (ii) in said process is preferably carried out according to the following operating conditions:

1') detaching the cells of the colonies formed from said dishes, by using conventional methods such as trypsinisation,
2') depositing said cells at a density preferably comprised between 1×10$^4$–5×10$^4$ cells/cm$^2$ onto new culture Petri dishes, already containing a number of pieces of the three dimensional matrix consisting of a derivative of hyaluronic acid, these pieces of hyaluronic acid derivative adhering to the culture dishes by the addition of human plasma fibrin at the interface hyaluronic acid derivative-Petri dishes.

The medium utilized in step (iii) is chosen in function of the type of differentiation bone marrow stem cells are to be subjected to.

For example when stem cells are to be partially or completely differentiated into fibroblasts, said medium does not contain any differentianting factor, but preferably a fibroblasts growth factor such as bFGF (basic Fibroblast Growth Factor).

In this case a partial differentiation already occurs before stem cells are transferred onto the three dimensional matrix.

When stem cells are to be partially or completely differentiated into chondrocytes, this medium preferably contains α-MEM supplemented with 10% foetal calf serum, 1% L-glutamin 200 mM, 1% penicillin-streptomycin 10,000 U/10,000 µg/ml, 50 µg/ml/day ascorbic acid, 100–1000 nM dexamethasone. This medium is preferably changed twice a week. Alternatively the medium contains Ham's F12 supplemented with 10% foetal calf serum, 1% L-glutamin 200 mM, 1% penicyllin/streptomycin 10,000 U/10,000 µg/ml/day, 50 µg/ml/day ascorbic acid, 2% ethanol.

When stem cells are to be partially or completely differentiated into osteoblasts step (ii) namely the transfer of stem cells onto the three dimensional matrix occurs on said matrix previuously treated with water containing hydroxy-apatite.

The medium in this case contemplated for step (iii) is α-MEM supplemented with 10% foetal calf serum, 1% L glutamin 200 mM, 1% penicyllin-streptomycin 10,000 U/10,000 µg/ml, 50 µg/ml/day ascorbic acid, 10–100 nM dexamethasone.

The step (iv), namely the osmotic lysis, for obtaining the component (a') is preferably carried out by using a solution of 5% deoxycholate. Also in the process for preparing the biologic material containing the the component (a') secreted by mature connective tissue cells, step (iv') namely the osmotic lysis is preferably carried out by using the aforementioned dexycholate solution. The biologic material according to the present invention can be cryopreserved so that a tissue bank can be built up to supply graft materials, or supports for keratynocytes cultures.

As a consequence of that each of the aforesaid processes for preparing the above mentioned biologic materials further comprise the final step consisting of cryopreserving according to conventional manner the obtained biologic material.

For purely indicative purposes, we present hereafter a few examples of the characterization of newly-formed tissue.

EXAMPLE 1

Isolation and Culture of Stem Cells

About 5–10 ml of bone marrow is aspirated from the iliac crest or head of femur.

The liquid, which also contains stromal bone fragments is placed in a 50 ml sterile tube and supplemented with 20–25 ml of Hank's saline solution at +4° C. The tube is centrifuged at approximately 1000 rpm for 5 minutes to eliminate the supernatant and the lipid layer, which are then aspirated. The excess of erythrocytes is eliminated by using Percoll ot Ficoll type gradients, after which the fraction containing mesenchymal cells is removed and centrifuged at 1000 rpm for 5 minutes. The pellet is resuspended removed and centrifuged in 5 ml culture medium (α-MEM supplemented with foetalclaf serum, 1% L-glutamine 200 mM, 1% penicillin/streptomycin 10,000 U/10,000 µg/ml) and seeded in Petri dishes with a diameter of 100 mm at a density of 50–100×10$^6$ nucleate cells/dish.

EXAMPLE 2

Transfer of Stem Cells in a Three Dimensional Matrix Consisting of HYAFF$^R$ 11 and HYAFF11 P75 and Differentiation of Stem Cells into Fibroblasts The cells are then left to incubate (37° C., pCO$_2$ about 5%) for 72 hours, after which the medium is changed in order to remove any non adhered cells. The mesenchymal cells remaining on the dish can be amplified by further passages (generally split ratio 1:3) and trasferred to a non woven tissue matrices of HYAFF$^R$-11 and HYAFF$^R$ 11p75, adding growth factor bFGF (1 ng/ml) to the culture medium. Some time later (1–2 weeks) the cells inside the biomaterial take on a fibroblast appearance and express phenotype typical of fibroblasts with the production of typical molecules of the connective matrix collagen type I, II, III, IV, fibronectin, laminin).

EXAMPLE 3

Preparation of:
Dermis α Containing:
   fibroblasts from bone marrow stem cells
   three dimensional matrix consisting of nonwoven HYAFF$^R$ 11
dermis α' (Control) Containing
   fibroblasts coming from human dermis
   three dimensional matrix consisting of nonwoven HYAFF$^R$ 11
Dermis β Containing
   fibroblasts from bone marrow stem cells
   three dimensional matrix consisting of nonwoven HYAFF$^R$ 11 p75
Dermis β' (Control) Containing
   fibroblasts coming from human dermis
   three dimensional matrix consisting of nonwoven HYAFF$^R$ 11 p75

Pieces of tissue (1.5×1.5 cm) comprised of both HYAFF$^R$ 11p75 and HYAFF$^R$ 11, are separately attached onto culture dishes by means of a fibrin clot. Human fibroblasts obtained from skin explants or from mesenchymal stem cells from bone marrow isolated and grown as described in Example 1 are separately seeded on the biomaterial at a density of $10^4$ cells×cm$^2$ in 0.2 ml of medium, soaking the biomaterial slowly. After about 30 minutes, DMEM culture medium complete with 10% FCS and 50 µg/ml of 1-ascorbic acid are added and the dishes are incubated at 37° C.

The medium is changed every 48 hours and the cultures are observed by phase-contrast microscope.

The pieces of biomaterial made of HYAFF$^R$ 11p75 can be cultured only for 7 days and since it it has been seen that, in the case of fibroblast cultures on HYAFF-11p75, the biomaterial begins to dissolve in the medium after 7 days. HYAFF-11, on the other hand, can be kept in culture for much longer (about 6 weeks). In this case, the pieces of HYAFF-11 are incubated with the cells for periods of 7, 14 and 21 days.

At the end of the culture period, the matrices of hyaluronic acid benzylester HYAFF$^R$ 11 p75 and HYAFF$^R$ 11, containing the fibroblasts from stem cells and the corresponding ones containing fibroblasts from human skin are detached from the dish without using lithic enzymes and divided into two parts.

One is fixed in formalin for routine histological tests and the other is frozen in liquid nitrogen and stored for subsequent immunohistochemical investigation.

The pieces fixed in formalin are stained with hematoxylin/eosine or by van Gieson's method, while the frozen material is stained immunohistochemically with mono- or polyclonal antibodies to show the presence of: fibronectin, collagen I, II and IV, laminin.

Results of Histological Staining
Hematoxylin/eosin

Elongated cells with typical fibroblast morphology are observed both in HYAFF$^R$ 11p75 and HYAFF$^R$ 11 biomaterials. From a morphological point of view, the fibroblasts obtained from dermis and those obtained from bone marrow mesenchymal cells are similar in appearance. In the case of HYAFF$^R$ 11, the fibres of the biomaterial are well preserved, while the HYAFF$^R$ 11p75 fibres show signs of disintegration.

Analysis of the biomaterial shows the presence of a delicate mesh of fine fibrils which turn pale pinkish red on staining with the Van Gieson method, confirming that they are collagen fibrils neosynthesized by the fibroblasts.

Immunohistochemical Characterization

The following antibodies were used to reveal the most representative molecules in the extracellular matrix:
1) human I anticollagen monoclonal antibodies
2) human III anticollagen monoclonal antibodies
3) human IV anticollagen monoclonal antibodies
4) human antifibronectin monoclonal antibodies
5) human antilaminin monoclonal antibodies The extracellular matrix deposited by the fibroblasts, both of dermal and bone marrow mesenchymal derivation, proved to be positive to the above immunoreactions. In particular, a notable fibrillar collagen (I and III) component was observed, as well as collagen IV. The typical adhesive molecules, fibronectin and laminin, which are characteristic of dermal tissue, are clearly expressed by these fibroblast cells, showing that a complete extracellular scaffold can be constituted within the matrices used by the Applicant.

EXAMPLE 4

Cryopreservation of Dermis α and Dermis β
Prepared as Described in Example 3

In order to demonstrate the possibility of preserving the artificial dermis obtained from stem cell culture in cold storage, the pieces of biomaterial containing the cells were frozen in the presence of a cold storage agent (dimethylsulfoxide, DMSO). The cultures were removed and placed in capsules containing DMEM, FCS and 10% DMSO, cooled to 4° C. and then frozen to −80° C. 5 minutes later.

One week later, the pieces of HYAFF$^R$ 11p75 are thawed from frozen and rapidly heated to 37° C., washed several times with DMEM with 10% FCS in order to eliminate the DMSO. They are left in an incubator for 24 hours, after which the cultures are transferred onto new pieces of HYAFF$^R$ 11p75 biomaterial of the same dimensions, which had been attached to culture dishes. This step is necessary to provide the cells with a new support, as the original nonwoven tissue starts to dissolve in the medium after 7 days.

The pieces of HYAFF$^R$ 11, on the other hand, are reused for culture after freezing in the conditions described above. All the thawed biomaterials are cultured for 7 days and then analysed as described in example 1. These new findings are similar to those described in example 1 and the tests performed with trypan blue staining show that the cells present in the HYAFF$^R$ 11 matrix are still viable after thawing.

FIGS. 1–5/A–B show histological photographs of the HYAFF$^R$ 11 nonwoven biomaterial wherein human fibroblasts from bone marrow and dermis have been seeded. Each figure describes the relative immunolocalization of collagen I, III, IV, fibronectin and laminin.

The various biomaterials made of HYAFF$^R$ 11 and HYAFF$^R$ 11p75 (gauzes, sponges, membranes) do not differ in any substantial way one from the other as far as fibroblast growth and the deposit of extracellular matrix is concerned.

EXAMPLE 5

Biological Material Coming from the Lysis of the Cellular Component of Dermis α, α', β and β'

The possibility of obtaining matrices of artificial dermis in vitro by the above-described method, with subsequent removal of the cellular component, was assessed as follows:

After the culture process described in Examples 1 and 2, the pieces of HYAFF$^R$ biomaterial are treated with distilled water and then with 5% sodium deoxycholate to lyse the fibroblasts present. These two treatments lead to cellular lysis and solubilization of the membranes, leaving the extracellular component more or less intact. Subsequent to this treatment, the histological and immunohistological examination of the pieces of biomaterial is performed as described in the previous examples.

Staining of the extracellular matrix with the specific antibodies shows that the procedure of elimination of the cellular component does not alter the architecture or composition of the extracellular matrix, which appears similar in all respects to that of the starting matrix, before cells removal.

EXAMPLE 6

Conditions for the Promotion of Stem Cell Differentiation Towards Chondrogenesis Stem cells, isolated as described in Example 1, are placed on matrices of non woven HYAFF$^R$ 11 and grown in a culture medium with a special composition: α-MEM supplemented with 10% foetal calf serum, 1% L-glutamin 200 mM, 1% penicillin/streptomycin 10,000U/10,000 μg/ml, 50 μg/ml/day ascorbic acid, 100–1000 nM dexamethasone. The cells are seeded at high concentrations (mass culture technique): at a mean density of $5-10^4$ cells/cm$^2$. The culture medium is normally changed twice a week. Alternatively, the following medium can be used: Ham's F12 supplemented with foetal calf serum, 1% L-glutamin 200 mM, 1% penicillin/streptomycin 10,000U/10,000 μg/ml, 50 μg/ml/day ascorbic acid, 2% ethanol.

Suitable phenotypic (chondrocyte) expression is monitored as follows:

morphological observation with an optical microscope;

specific staining of histological specimens with Alcian blue, toluidine blue and type II anti-collagen monoclonal antibodies;

quantifications of the supernatant for the production of glycosaminoglycans and type II collagen.

In both the culture medium supplemented with dexamethasone and in that containing 2% ethanol, a high percentage of differentiation of the stem cells towards chondrocytes can be observed.

EXAMPLE 7

Conditions for the Promotion of Stem Cell Differentiation Towards Osteogenesis

In order to promote differentiation towards osteogenesis mesenchymal cells are grown on non-woven HYAFF$^R$ 11 with the following culture medium: α-MEM supplemented with 10% foetal calf serum, 1% L-glutamin 200 mM, 1% penicillin/streptomycin 10,000U/10,000 μg/ml, 50 μg/ml/day ascorbic acid, 10–100 nM dexamethasone.

Before seeding, the HYAFF$^R$ 11 material is treated for 12–24 hours with water containing hydroxy-apatite. The culture medium is normally changed twice a week.

Suitable phenotypic (osteocyte) expression is monitored by:

morphological observation with an optical microscope;

specific staining of histological specimens according to Von Kossa;

histochemical staining to reveal the presence alkaline phsosphatase activity.

In these experimental conditions it is possible to observe how the presence of hydroxy-apatite crystals in the HYAFF$^R$ 11 induces the mesenchymal cells towards osteocytes.

What is claimed is:

1. A biological material comprising the following two components:

(a) a first component comprising:

(1) a culture of autologous or homologous bone marrow stem cells partially or completely differentiated into cellular lines of a specific connective tissue selected from the group consisting of fibroblasts, osteoblasts, myoblasts, adipocytes, chondrocytes and endothelial cells and an extracellular matrix produced by the specific connective tissue cellular lines, or, alternatively (2) a sole extracellular matrix free from any cellular component secreted by said specific connective tissue cellular lines resulting from partially or completely differentiated bone marrow stem cells, or secreted by specific mature connective tissue cells selected from the group consisting of fibroblasts, osteoblasts, myoblasts, adipocytes, chondrocytes and endothelial cells; and (b) a second component comprising a three-dimensional biocompatible and biodegradable matrix consisting of a hyaluronic acid ester having a degree of esterification comprised between 25 and 100%.

2. The biological material according to claim 1, wherein the component (b) is in the form of non-woven tissue, sponges, granules, microspheres, guide channels and gauzes.

3. The biological material according to claim 2, wherein the component (b) is in the form of a non-woven tissue.

4. The biological material according to claim 1, wherein the degree of esterification is 75% or 100%.

5. The biological material according to claim 1, wherein said extracellular matrix of (2) is secreted by a homologous cellular culture.

6. The biological material according to claim 1, wherein the hyaluronic acid ester is a benzyl ester.

7. A method for repairing a damaged connective tissue, selected from the group consisting of bone, cartilage, dermal, muscular, adipose and endothelial tissue, comprising applying to a patient in need of such a treatment the biological material of claim 1.

8. The method according to claim 7 for treating areas with eroded or degenerated cartilage wherein the biological material contains culture (1) comprising bone marrow stem cells partially or completely differentiated into chondrocytes.

9. The method according to claim 7 for treating loss of bone substance wherein the biological material contains culture (1), comprising bone marrow stem cells partially or completely differentiated into osteoblasts.

10. The method according to claim 7 for grafting autologous or homologous keratinocytes wherein the biological material contains culture (1), comprising bone marrow stem cells partially or completely differentiated into fibroblasts, said biological material being previously in vitro seeded with keratinocytes prior to grafting.

11. The method according to claim 7 for treating conditions in need of a dermal substitute wherein the biological material contains extracellular matrix (2), secreted by bone marrow stem cells partially or completely differentiated into fibroblasts.

12. The method according to claim 7 for treating areas with eroded or degenerated cartilage wherein the biological material contains extracellular matrix (2), consisting of an extracellular matrix secreted by mature connective tissue cells comprising chondrocytes.

13. The method according to claim 7 for treating loss of bone substance wherein the biological material contains extracellular matrix (2), consisting of an extracellular matrix secreted by mature connective tissue cells comprising osteoblasts.

14. The method according to claim 7 for grafting autologous or homologous keratinocytes wherein the biological material contains extracellular matrix (2), consisting of an extracellular matrix secreted by mature connective tissue cells comprising fibroblasts, said biological material being previously in vitro seeded with keratinocytes prior to grafting.

15. The method according to claim 7 for grafting a dormal substitute wherein the biological material contains extracellular matrix (2), consisting of an extracellular matrix secreted by mature connective tissue cells comprising fibroblasts.

16. The method according to claim 7 for treating areas with eroded or degenerated cartilage wherein the biological material contains extracellular matrix (2) consisting of an extracellular matrix secreted by bone marrow stem cells partially or completely differentiated into mature connective tissue cells comprising chondrocytes.

17. The method according to claim 7 for treating loss of bone substance wherein the biological material contains extracellular matrix (2), consisting of an extracellular matrix secreted by bone marrow stem cells partially or completely differentiated into mature connective tissue cells comprising osteoblasts.

18. The method according to claim 7 for grafting autologous or homologous keratinocytes, wherein the biological material contains extracellular matrix (2), consisting of an extracellular matrix secreted by bone marrow stem cells partially or completely differentiated into mature connective tissue cells comprising fibroblasts, said biological material being previously in vitro seeded with keratinocytes prior to grafting.

19. The method according to claim 7 for grafting a dermal substitute wherein the biological material contains extracellular matrix (2) consisting of an extracellular matrix secreted by bone marrow stem cells partially or completely differentiated into mature connective tissue cells comprising fibroblasts.

* * * * *